(12) United States Patent
Fendell (10) Patent No.: US 9,977,963 B1
(45) Date of Patent: May 22, 2018

(54) UAVS FOR TRACKING THE GROWTH OF LARGE-AREA WILDLAND FIRES

(71) Applicant: NORTHROP GRUMMAN SYSTEMS CORPORATION, Falls Church, VA (US)

(72) Inventor: Francis E. Fendell, Los Angeles, CA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 0 days. days.

(21) Appl. No.: 15/449,021

(22) Filed: Mar. 3, 2017

(51) Int. Cl.
| | |
|---|---|
| *G06K 9/00* | (2006.01) |
| *G01P 5/00* | (2006.01) |
| *G01J 5/00* | (2006.01) |
| *G01C 11/02* | (2006.01) |
| *G05D 1/00* | (2006.01) |
| *G01N 21/01* | (2006.01) |

(52) U.S. Cl.
CPC ............ *G06K 9/0063* (2013.01); *G01C 11/02* (2013.01); *G01J 5/0014* (2013.01); *G01N 21/01* (2013.01); *G01P 5/001* (2013.01); *G05D 1/0011* (2013.01); *B64C 2201/021* (2013.01)

(58) Field of Classification Search
CPC ... B64C 39/024; A62C 3/0271; G08B 17/005; G08B 17/125
See application file for complete search history.

(56) References Cited

U.S. PATENT DOCUMENTS

| 9,665,094 B1 * | 5/2017 | Russell | ................... G05D 1/00 |
| 2005/0139363 A1 * | 6/2005 | Thomas | ................ A62C 3/025 169/30 |

(Continued)

OTHER PUBLICATIONS

Peace, Mika et al. "Fire-Modified Meteorology in a Coupled Fire-Atmosphere Model" Journal of Applied Meteorology and Climatology, vol. 54, American Meteorological Society 2015, pp. 704-720.

(Continued)

*Primary Examiner* — Bhavesh Mehta
*Assistant Examiner* — Ian Lemieux
(74) *Attorney, Agent, or Firm* — John A. Miller; Shumaker, Loop & Kendrick, LLP (57) ABSTRACT

A system and method for tracking the growth of large-area wildland fires. The technique includes monitoring wind conditions in and around a wildfire using near-surface-sited sensors deployed by a high-altitude long-endurance (HALE) unmanned aerial vehicle (UAV), such as the Global Hawk. The deployed sensors measure a localized wind vector at multiple locations within and surrounding the wildfire, and transmit the wind data back to the UAV for relaying to a command center operated by fire management authorities, where the wind data are used to assist decision-making, including as input into wildfire growth prediction models. The sensors may provide additional data such as local altitude/elevation, pressure, temperature and relative humidity. The UAV may also carry sensors that provide additional data to be used by the fire management authorities or the wildfire growth prediction models—such as infrared images defining actively flaming areas, and visual images which indicate vegetation type and density.

19 Claims, 4 Drawing Sheets

(56) References Cited

U.S. PATENT DOCUMENTS

| | | | | |
|---|---|---|---|---|
| 2009/0326792 | A1* | 12/2009 | McGrath | G01W 1/08 701/120 |
| 2010/0070111 | A1* | 3/2010 | Akcasu | A62C 3/025 701/3 |
| 2012/0261144 | A1* | 10/2012 | Vian | G06Q 10/06315 169/43 |
| 2014/0027131 | A1 | 1/2014 | Kawiecki | |
| 2014/0077969 | A1* | 3/2014 | Vian | H04Q 9/00 340/870.02 |
| 2016/0112854 | A1* | 4/2016 | Goossen | H04W 4/22 455/404.2 |
| 2016/0247404 | A1* | 8/2016 | Srivastava | G01C 21/20 |

OTHER PUBLICATIONS

Fendell, Frank et al. "Fire-Growth Prediction for Complex Topography by Level-Set Methods: Synthetic and Mesonet-Based Flows" Final Report through Northrop Grumman, Sep. 30, 2014, 45 pgs.

Coen, Janice L. et al. "Simulation and Thermal Imaging of the 2006 Esperanza Wildfire in Southern California: Application of a Coupled Weather-Wildland Fire Model" International Journal of Wildland Fire, 2014, pp. 755-770.

Mallet, V. et al. "Modeling Wildland Fire Propagation with Level Set Methods" Computers and Mathematics with Applications 57, 2009, pp. 1089-1101.

* cited by examiner

UAVS FOR TRACKING THE GROWTH OF LARGE-AREA WILDLAND FIRES

BACKGROUND

Field

This invention relates generally to a system and method for tracking the growth of large-area wildland fires and, more particularly, to a system and method for sustained and continuous monitoring of wind conditions in and around a wildfire using near-surface-sited sensors deployed by an unmanned aerial vehicle (UAV), where the sensors measure a localized wind vector at multiple locations within and around the wildfire, and the sensors transmit the wind data back to the UAV for relaying to a user of the wind data to assist in decision-making with the aid of wildfire growth prediction models.

Discussion

Wildland fires, commonly called wildfires, may be caused naturally (as by lightning) or may be human-caused—where human-caused wildfires may be accidentally set, intentionally set by an arsonist, or intentionally set for purposes of a "controlled" burn for fuel reduction in a wildland. Regardless of the cause of a wildfire, it is essential that the fire be managed until it is extinguished. As interpreted here, management of a wildfire may include passive monitoring to an expected acceptable conclusion, controlling the extent of the burn using firebreaks or backfires, retarding spread of or extinguishing parts or all of the fire with water, dirt and/or chemicals, or a combination of these approaches. Whatever the cause of ignition of a wildfire, it may be determined that the most appropriate response is to let it burn, if no danger to life or property is posed by the fire.

To monitor and manage a wildfire effectively, it is advantageous to have accurate information about the conditions around and within the fire. In particular, the rate of firefront advance into previously uninvolved vegetation (the rate of firespread) depends on topography, vegetation and meteorology. Topography is generally known, and typically changes only over thousands or millions of years. Vegetation changes mainly seasonally, and vegetation conditions (sparse or thick, old or new growth, dry or moist, surface or crown, mixed-species or homogeneous) are generally fairly well-known or reasonably approximated in fire-prone regions. However, meteorology (especially the wind speed and direction) can change appreciably in a span of 10 minutes or so. Thus, in general, the critical, short-term variable for wildland-fire behavior is wind; a wildland-fire crisis typically arises, persists, and decays as a strong wind arises, persists, and decays. Furthermore, level topography (flat land) tends to be reserved for development and agriculture, and wildlands are often characterized by complicated terrain which can appreciably affect local wind patterns. Knowledge of the current and near-term wind speed and direction a meter or two above the ground or shrub vegetation (the wind field pertinent to firespread through "surface" vegetation) remains a challenge in complicated terrain, as there typically are no pre-deployed weather stations at these often remote sites.

In order to improve the tracking and growth prediction of wildfires, especially large-area wildland fires, a means of providing, on demand, detailed, accurate, real-time, near-surface wind data in and around the fires is needed.

SUMMARY

The present invention discloses and describes a system and method for tracking the growth of large-area wildland fires. The technique includes monitoring wind conditions in and around a wildfire using near-surface-sited sensors deployed by a high-altitude long-endurance (HALE) unmanned aerial vehicle (UAV), such as the Global Hawk. The sensors measure a localized wind vector at multiple fixed locations within and surrounding the wildfire, and the sensors transmit the wind data back to the UAV for relaying to a fire-incident command center operated by fire management authorities, where the wind data may be used either intuitively or as key input in wildfire growth prediction models. The sensors may provide additional data such as local altitude/elevation, pressure, temperature and relative humidity. The UAV may also carry and power additional onboard sensors which provide additional data to be used by the fire management authorities or the wildfire growth prediction models—such as infrared images defining actively flaming areas, and visual images which indicate vegetation type and density.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a system and method for tracking growth of a wildfire using a UAV is merely exemplary in nature, and is in no way intended to limit the invention or its applications or uses. For example, as discussed herein, the system and method have particular application for detecting and tracking a large-area wildland fire. However, the system and method discussed herein may have application for detecting and tracking other types of events, such as oil spills in coastal waters.

Wildland fires, or wildfires, may be beneficial to ecosystems when they burn combustible vegetation not too intensely; they burn off undesirably dense vegetation, release nutrients, allow regrowth of native grasses and forbs and otherwise support regeneration, and fight the spread of infestations through vegetation. On the other hand, wildfires can be enormously destructive (to the scale of single-incident billion-dollar loss of assets) and hazardous to wildlife and humans, resulting in degradation of air quality and visibility and watershed quality, and even in loss of life.

Wildland-firefighting crews typically possess the experience and expertise to deal with a nascent uncontrolled fire if they can gain access, and generally require no input from "high technology". However, if a burn evolves to develop a well-defined high-intensity firefront, such that vigorous flaming of thermally and physically thin vegetation in a narrow, roughly 10-meter-thick strip separates an expanse of mostly burned vegetation, located to one side of the strip, from an expanse of unburned vegetation to the other side, then assistance with anticipating the fire behavior is typically useful to respondents. This holds for both "controlled" fuel-reduction burns, and for unplanned lightning-or-anthropogenically-initiated burns. A key question becomes: given where the actively flaming firefront is currently located, where will the firefront be situated in a few hours' time, both with and without firefighting intervention. A longer time horizon for prediction would be desirable, of course, but may not be physically accessible.

Accurate prediction of firespread (i.e., anticipating what vegetation will burn when, and how completely) is prerequisite to prediction of most other fire effects (smoke/soot/ash transport, air-quality and visibility degradation, etc.). Firespread prediction is also crucial to decision-making about whether to deploy, and, if so, how to deploy most cost-effectively and safely, firefighting assets (manpower, ground equipment, aerial resources, etc.). Issuance of red-flag warnings that conditions are present for dangerously rapid growth of fires is also dependent upon a prediction of firespread. Federal and state land managers and forest-resource managers will hesitate to adopt a "let it burn" option, even if virtually no valuable societal assets are at risk, without the backup of a validated fire-behavior tool. Such reluctance has appreciable cost to the environment and to the taxpayer.

Fast-running, real-time, firespread-growth-predictive tools (computer models) have been developed which can guide the decision-making of an Incident Commander (IC) regarding deployment of aircraft, ground-equipment, and hotshot-crew assets (or, alternatively, letting a fire burn under passive monitoring). The effects of fire management techniques may be simulated in the models, including: water/retardant drops may be modeled by modification of fuel-moisture content; cutting lines, by modification of fuel-loading distribution; and backfiring, by ignition of fresh firestarts in the vicinity of an existing-fire perimeter. Thus, the relative merits of undertaking alternative countermeasures may be evaluated.

In addition, the potential utilization of a fast-running wildland-firespread tool for community planning (layout of firebreaks, roads, reservoirs, structures), guiding evacuation decisions, fire-litigation support, and training and certification of personnel indicates that the firespread model has practical value as a pre-crisis, in-crisis, and post-crisis aid. However, the many benefits of firespread prediction modeling are available only if accurate setting-descriptive parameters are available as inputs to the model—including topography, vegetation and meteorology. Of these, meteorology—particularly, local wind speed and direction in and around the wildfire—traditionally has been especially difficult to characterize accurately.

Figure 1:
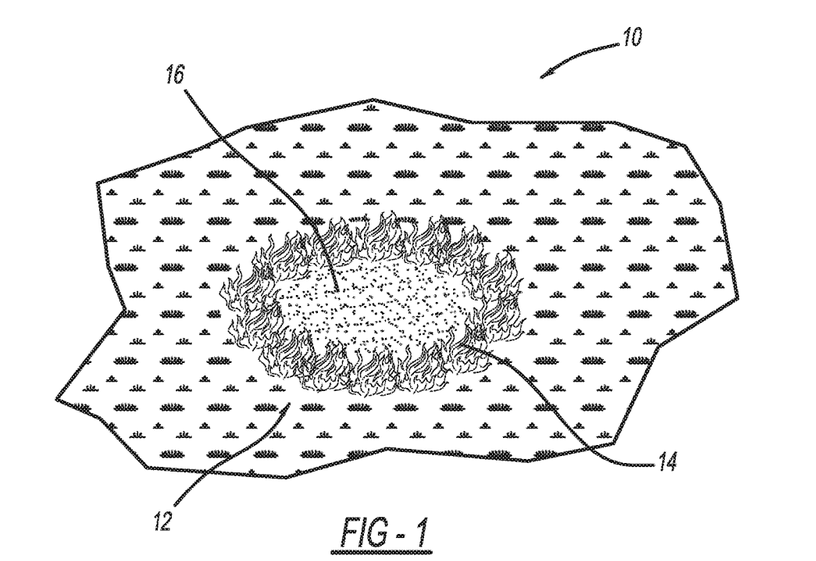
FIG. 1 is a simple illustration of growth of a wildfire in no-wind conditions.

FIG. 1 is a simple illustration 10 of growth of a wildfire 12 in no-wind conditions, with no-wind conditions henceforth denoting no-ambient-wind conditions. The wildfire 12 includes a burning area 14 around its perimeter, and an already-burned area 16 at its core. The burning area 14, as the name implies, has actively-flaming combustible material. The burned area 16 has been transformed mainly to smoldering ash and char, and thicker vegetation that does not burn with firefront passage. As would be understood by one skilled in the art—if topography is flat and vegetation is uniform to fairly fine spatial scale, the wildfire 12 in no-wind conditions takes on a generally circular shape, with the burning area 14 being a substantially uniform band around the perimeter of the burned area 16. Furthermore, the flame intensity and growth rate of the wildfire 12 are modest owing to the lack of flame-fanning winds to abet ignition of previously uninvolved vegetation. Unfortunately, unlike contrived experiments, real-world wildland fires rarely if ever behave as represented by the no-wind wildfire 12 of FIG. 1.

Figure 2:
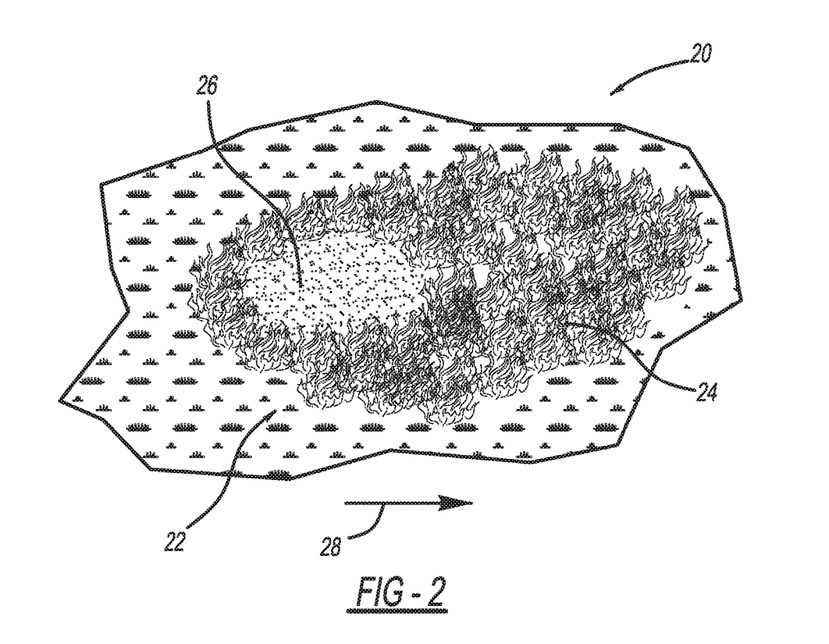
FIG. 2 is a simple illustration of growth of a wildfire in conditions in which a wind is present.

FIG. 2 is a simple illustration 20 of growth of a wildfire 22 for conditions in which a wind is present. The wildfire 22 includes a burning area 24 and a burned area 26, as discussed above. The wind direction is designated by a vector 28. Owing to the wind, the perimeter of the wildfire 22 often takes on a generally elliptical shape, with the burning area 24 being larger and more intense ahead (i.e., downwind) of the burned area 26. Furthermore, the flame intensity and growth rate of the wildfire 22 are greater than those of the wildfire 12 owing to the flame-fanning winds.

The simplified discussion of FIGS. 1-2 above highlights the importance of knowing wind conditions to predict growth of a wildfire. Wildland fires, by definition, occur in undeveloped terrain such as national parks and forests, where there are typically no weather sensors present. Even in the currently most extensive installations of surface-weather sensors over a large area in the United States—such as in Orange and San Diego Counties of southern California—the grid of sensors is far too coarse to be of much use in fire growth prediction. For example, the southern California grid has sensors placed several miles apart in each direction. It would be cost-prohibitive to install permanent, self-powered, surface-sited wind/weather sensors, with signal-activated centralized readout, on a fine-scale grid (many per square mile) over, for example, the entire western United States—a region which is historically prone to wildfires. What is practical instead is a network of near-surface wind sensors which is rapidly deployable on demand, exactly where it is needed in the event of a large-area wildland fire. The wind data from such deployable, on-demand sensors could then serve as the source for key, currently unavailable input data, for example, for fire growth prediction models.

As will be discussed in detail below, the present invention proposes using an unmanned aerial vehicle (UAV), such as the Northrop Grumman Global Hawk, which flies above a wildfire and deploys many wind sensors within the wildfire and the surrounding area. The UAV continues to fly above the wildfire for an extended period of time, collecting and relaying the wind data from the near-surface-deployed sensors, and providing other data such as imagery of the fire which may be helpful in tracking and "nowcasting" fire growth. The UAV provides a high-altitude, long-endurance (HALE) vehicle that allows real-time monitoring of a wildfire's growth. This is done, in the case of the Global Hawk, through the combination of fast-flying, high-flying, long-mission, large-payload, large-on-board-power-supply, real-time-data-readout, and in-flight-mission-re-direction capabilities, along with multiple bays, pods, and hard points to accommodate a wide range of remote-sensing and in situ payloads.

Figure 3:
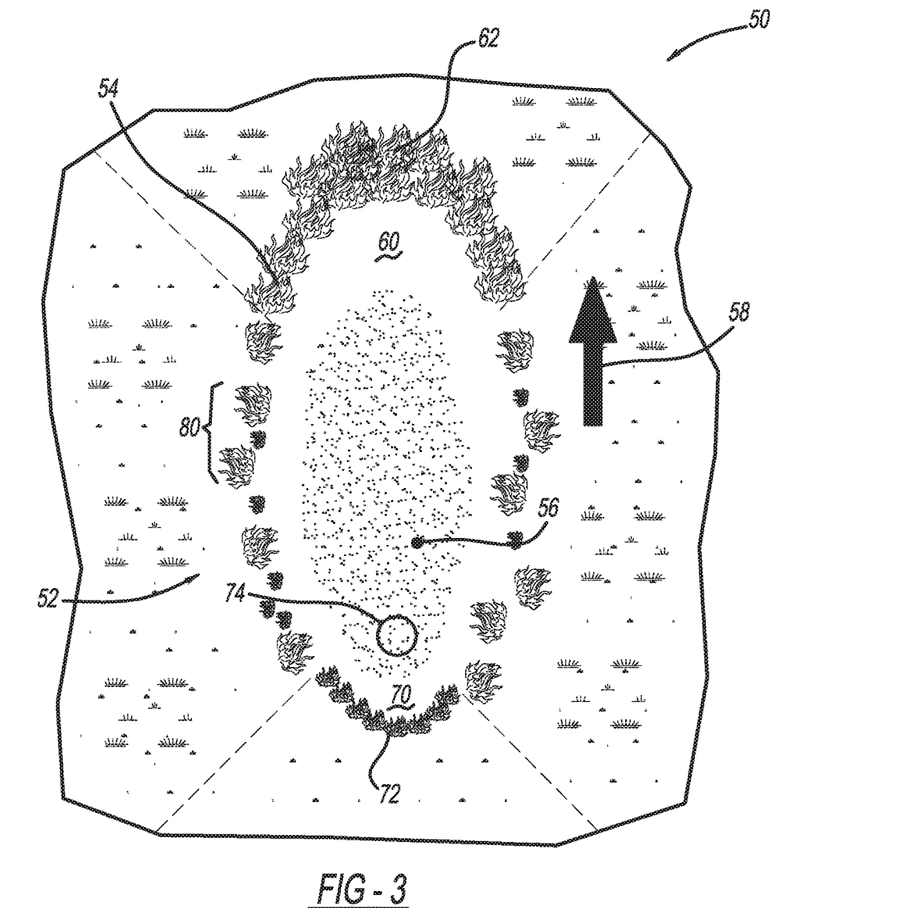
FIG. 3 is an illustration of growth of a wildfire in conditions in which a wind is present, showing parts of the wildfire and how they typically behave.

FIG. 3 is an illustration 50 of growth of a wildfire 52 for conditions in which a wind is present, showing parts of the wildfire and how they typically behave. The wildfire 52 includes a burning area 54 and a burned area 56, as discussed above. Similar to the discussion of FIG. 2 above, the wildfire 52 is being influenced by a wind designated by a vector 58. Each half of a mirror-image depiction of the wildfire 52 conceptually may be sub-divided roughly into three zones as indicated by the dashed lines in the illustration 50.

The wildfire 52 has a head 60 and heading fire 62 at its downwind end. The head 60 and heading fire 62 pertain to wind-assisted spread of the wildfire 52. The heading fire 62 is characterized by the most intense burning, with the flames often being tilted over unburned vegetation by the wind, to facilitate preheating and contact ignition, and thereby increase the rate of firespread. Furthermore, burning brands and embers can be blown downwind ahead of the heading fire 62 into unburned vegetation and effect ignition there, thereby increasing the rate of fire advance and possibly bypassing fuel-bereft firebreaks.

At the upwind end, opposite the head 60, is a back 70 with a backing fire 72. The backing fire 72 moves very slowly because fire spread is against the wind, i.e., wind-opposed. In the illustration 50, the wildfire 52 takes on a roughly elliptical shape, in which an ignition point 74 is much closer to the back 70 than the head 60 owing to the rapid advance of the head 60.

On the left and right sides of the wildfire 52 are flank fires 80. The flank fires 80 are moderate in intensity—nominally propagating mostly traverse to the prevailing wind direction. The flank fires 80 are sometimes characterized as alternately backing and heading fires owing to variable wind patterns within and around the wildfire 52.

Of course, the illustration 50 of FIG. 3 is a highly simplified depiction of a wildfire, as physically encountered wildfires involve complicated terrain, uneven heterogeneous vegetation, variable wind speed and direction, and other complications such as inert rocks and streams. Indeed, many tragic incidents involving firefighters result from the interaction of terrain and wind speed/direction such that the back and head, or a flank and head, interchange position abruptly.

It is emphasized that the elliptical shape of the wildfire 52 is a generalization, a shape which is approximated only in some real world fires. A real world fire is never going to be completely uniform, and instead will include varying intensities in the burning area 54, unburned patches around the perimeter, etc. Furthermore, the elliptical shape may evolve into an egg-shaped or other geometry, and some types of vegetation fires tend to produce burned areas which are more wedge-shaped. For some wildfires, a perimeter consisting of a simple closed curve may not exist at all.

However, by use of the basic concepts illustrated in FIG. 3 and advanced computational techniques, combustion models have been developed over the past several years, and physically encountered wildfires may be modeled to a usefully accurate approximation if input data are available. As discussed above, the input data for fire growth prediction models include topography, vegetation and meteorology. Although FIG. 3 shows the simple single wind vector 58, a physically encountered wildfire, particularly a large-area fire, may have widely varying wind speeds and directions at various locations at various times. An example of a significant near-surface wind generated by the fire itself is the sudden collapse of a particle-laden pyrocumulus cloud, with resulting significant laterally-outward flow from the site of collapse. Thus, a single-site, one-time reading of wind velocity is not sufficient to model accurately physically encountered wildfires, especially if the reading is for a site distant from the fire. What is needed instead is an array of many sensors, located within and surrounding a wildfire, continuously measuring and transmitting wind speed and direction in real time.

The rapid "runs" of wildland fires almost invariably involve wind-aided firespread, whether the mechanism of spread entails effectively continuous fire propagation to engulf fresh combustible elements, or discontinuous advance by downwind spot ignitions owing to firebrands and embers, or a combination of both. However, quantitative information concerning the pertinent, near-Earth-surface wind field in hilly terrain, in which wildland fire typically occurs, is rarely available. This major desiderata, impeding useful short-term forecasting in real time of fire growth and fire behavior for any locale of interest, may be achieved by the rapid, on-demand, optimally-sited deployment of a number of robust, temporarily-active weather stations. In particular, such deployment is feasible even for the often-relatively-remote sites where wildland fires often arise and escape any attempt at early suppression.

The reporting of a comprehensive set of a couple-dozen fire-related parameters describing atmospheric/vegetation/soil conditions would be desirable. Nevertheless, specifically helpful is the deployment of at least a few sensors, each capable of reporting wind speed and direction at several near-ground altitudes, but, as a minimum, at a height of a meter or so above ground or local surface-vegetation level. The data may be collected by virtually continuous transmission from each sensor to an overhead-circling collector, and then further transmission to a data-processing center, for subsequent distribution over established networks to user communities such as fire management authorities and firespread modeling specialists.

A feasible means of delivering/deploying and then monitoring such self-powered weather stations at a pre-specified remote site is a fast-flying, long-mission, heavy-payload-carrying, multi-payload-accommodating, high-altitude long-endurance (HALE) unmanned aerial vehicle (UAV). After sensor deployment, such a UAV is capable of signal collection and transmittal to end-user receivers. Throughout their Earthward descent, multiple dropsonde-type probes may continually communicate probe-sensor-collected data (values, location, time) to the circling UAV. Furthermore, in light of the priorities for wildfire wind measurement, the sensors as proposed herein come to rest on the ground and advantageously continue to measure and transmit fixed-position, near-surface wind data for many days after landing on the ground. The power required to transmit from the near-surface-sited sensors to the closer-proximity UAV—both during descent and after landing—is less than the power required to transmit to geosynchronous satellites.

Figure 4:
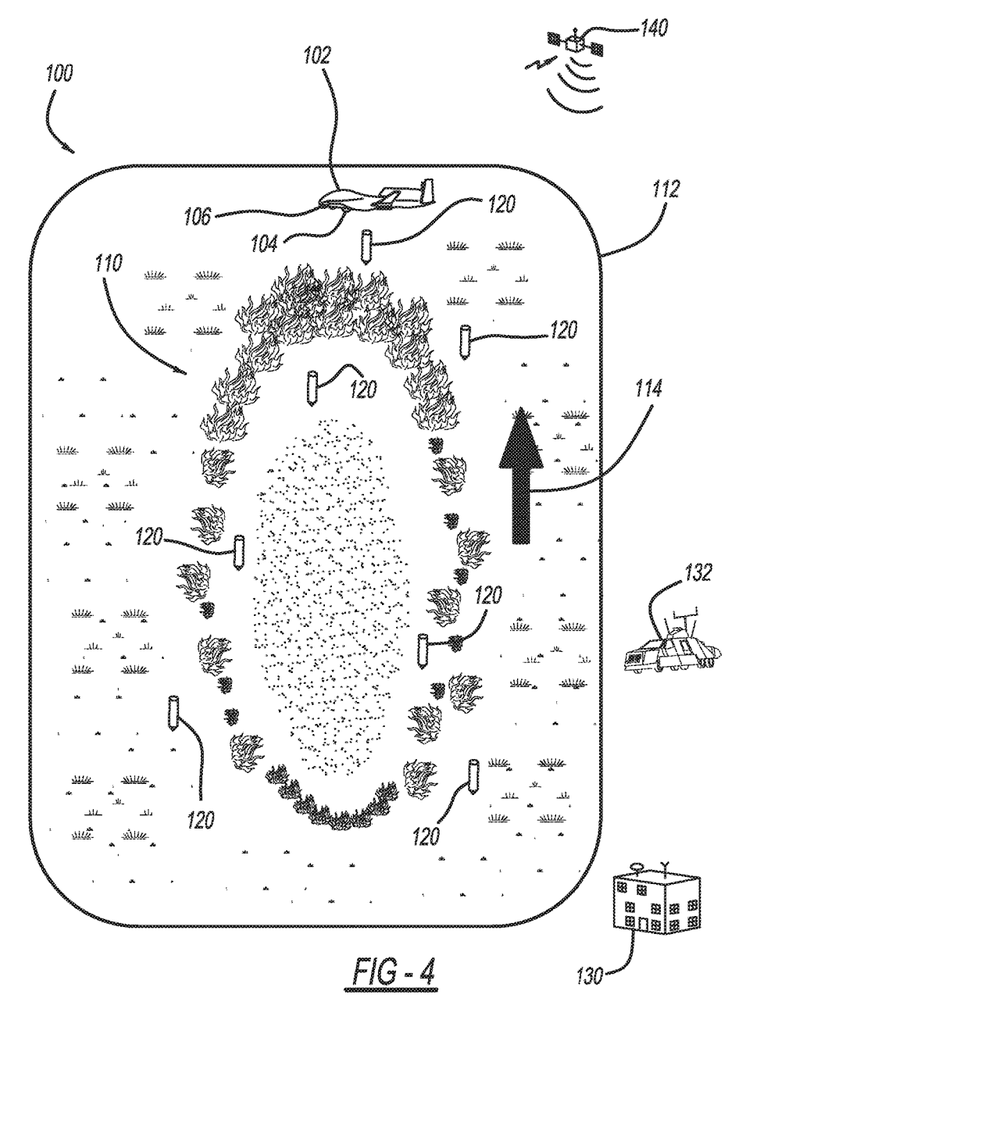
FIG. 4 is an illustration of a UAV flying above a wildland fire, such as the wildfire of FIG. 3, and deploying a plurality of near-surface-sited sensors to measure local wind conditions in and around the wildfire.

FIG. 4 is an illustration of a system 100 for providing real-time wind data for a wildfire, according to an embodiment of the present invention. The system 100 features a UAV 102 flying above a wildfire 110 and deploying a plurality of near-surface-sited sensors 120 to measure local wind conditions in and around the wildfire 110. A target area 112 is defined as an area encompassing the wildfire 110 and some surrounding area, anticipating expected wind and expected growth of the wildfire 110 based on an expected wind vector 114. The target area 112 is the area within which the near-surface-sited sensors 120 will be deployed, and may range in size from a fraction of a square kilometer up to several square kilometers. The near-surface-sited sensors 120 may be deployed in a somewhat random scattering over the target area 112, or the sensors 120 may be deployed by the UAV 102 in a predetermined pattern—such as a circular (single or multiple-concentric), oval or spiral pattern, or a rectangular grid. The UAV 102 can aim each of the deployed sensors 120 for a specific landing point based on the desired pattern and the drop parameters (UAV altitude and velocity, wind, and instrumentation-package aerodynamics). In any case, many of the sensors 120—at least a half dozen, and possibly two dozen or more for a large fire—are deployed by the UAV 102 over the target area 112. The more of the sensors 120 that are deployed, the better the resulting wind data quality should be—as local wind conditions can be and are affected by vegetation patterns (such as tall trees), topography (such as hills, valleys, ridges, etc.) and even by the fire itself. Three-dimensional interpolation/extrapolation of a solenoidal-model wind field obtained from data of a partial deployment of the sensors 120 may guide "optimized" positioning of subsequently deployed sensors.

Data transmissions from the near-surface-sited sensors 120 may be continuous, or may be intermittent at an interval of—for example—once every few seconds. In one embodiment, the near-surface-sited sensors 120 transmit their data to the UAV 102 circling overhead, which relays the data to a ground station (which may be a nearby ground station 130) or to a (preferably geosynchronous) satellite 140. An alternative is to have the near-surface-sited sensors 120 report their data directly to the nearby ground-based collection site 130 (e.g., on a hilltop) or a mobile ground-based collection vehicle 132, which then transmits the data directly to end users or to an overhead collector (the UAV 102 or the satellite 140). In any transmission/relaying route that may be chosen, the goal is reliable data transmission over a sufficiently short distance to allow relatively low power transmitters to be used in the near-surface-sited sensors 120. Regardless of the transmission route, the data from the sensors 120 ultimately are provided to fire management authorities—both for the personal knowledge of the Incident Commander and others, and for use in the computer-based growth prediction models. The near-surface-sited sensors 120 preferably transmit their data via radio frequency (RF) signals on a suitable frequency.

At a minimum, the near-surface-sited sensors 120 each provide wind speed, wind direction and sensor location data, along with a timestamp. The wind speed and direction data are collected using any suitable sensors and techniques, as would be understood by one skilled in the art. The sensor location data may be provided by an onboard GPS receiver on each of the near-surface-sited sensors 120, or by signal triangulation from the UAV 102. The sensor location data preferably include not only two-dimensional "map" location (such as latitude and longitude), but also elevation/altitude. Altitude data are useful during descent of the sensors 120, and elevation data are useful after sensor landing to provide precise validation of terrain maps (and also to indicate a problem such as one of the sensors 120 getting stuck in a tree or a fire-lookout structure during descent).

As mentioned above, the wind data that are most relevant to fire growth are measured at a height of 1-2 meters above ground or surface vegetation. In a preferred embodiment, the near-surface-sited sensors 120 are designed to position their wind sensor at this 1-2 meter height when the sensor 120 has landed on the ground. This may be done by designing the sensors 120 to be very bottom-heavy so as to remain upright after landing, with a light-weight superstructure (the sensor body, or a wire whip, etc.) supporting the wind sensor 1-2 meters above ground. Other design techniques may also be used to position the wind sensor at the desired height. The sensors 120 are also designed for a controlled, accurate descent from the UAV 102 to the ground. Aerodynamic features may include packaging shape, stabilizing and drag-inducing fins (as on a bomb), small drag parachutes or flaps, or other devices.

The near-surface-sited sensors 120 measure wind vectors at many locations within the target area 112 (each sensor providing wind data at one location, of course), thus providing much more detailed and accurate wind data than the single wind vector 114. Other data besides wind speed and direction may also be obtained by the UAV-deployed sensors 120. For example, air temperature, air pressure and relative humidity are all relevant to fire modeling, and may be measured by the sensors 120. In addition, soil moisture data are useful in wildfire modeling, and may be obtained by a moisture sensor on or protruding from the bottom of the sensor 120. Furthermore, although providing only a brief snapshot in comparison with the sustained data collection after landing, the near-surface-sited sensors 120 may also measure and transmit data during their descent from the UAV 102 to ground. Air temperature, pressure, humidity and wind data (along with altitude) through the depth of the troposphere (measured during descent) is particularly useful for smoke dispersion prediction. The UAV-deployed sensors 120 are designed to withstand the descent to earth and the effects of the wildfire 110 and, because they continue transmitting data including location, they may be readily found and retrieved after the wildfire event has concluded.

The Northrop Grumman Global Hawk is a high-altitude long-endurance (HALE) UAV ideally suited to the system 100. The Global Hawk cruises at a speed of around 350 miles per hour (mph), and can handle a payload of 2000 lb. or more. The high speed of the Global Hawk translates to short times enroute from airfield to wildfire and return, and thus more time spent "on mission" productively monitoring the wildfire. The high-altitude flight capability of the Global Hawk means that any intervening weather will not impede its access to the wildfire location. The large payload means that the Global Hawk can carry many of the sensors 120 and deploy them to the target area 112. In fact, the Global Hawk has sufficient payload capability and hard mounting points to carry and deploy dozens of the sensors 120, which is sufficient for almost any wildfire scenario.

Long endurance is another feature of the Global Hawk which meets the needs of wildfire monitoring. The Global Hawk has a flight endurance of 30-40 hours. Given the high flight speed of the Global Hawk which enables rapid arrival on target, the long flight endurance equates to a time on target of up to 30 hours, or more. These features allow a large-area wildfire which persists for days or even weeks to be continuously monitored by just two of the Global Hawks, where there is ample time to refuel, perform maintenance, and restock one unit while the other unit is in flight. It is also envisioned that more of the sensors 120 will need to be deployed at some time after the initial deployment, as the target area 112 will shift or grow, or the self-power capacity of the deployed sensors will be exhausted. The long time on mission capability of the Global Hawk allows the UAV 102 to be selective about sensor deployment sites in response to unanticipated fire behavior.

The UAV 102 may also collect and transmit other data with onboard sensors, independently of the dropsonde sensors 120. For example, infrared images of the target area 112 may be taken by an infrared sensor 104, where the infrared images are valuable for identifying the location and intensity of active flaming in the wildfire 110, even through smoke, ash or clouds. Infrared imagery of near-surface flaming is particularly well defined at night, so the long duration on target of the Global Hawk is helpful. Visual images of the target area 112 may also be taken by a camera 106, where the visual images are valuable for determining the shape of the wildfire 110 and its smoke plume, and determining vegetation conditions surrounding the wildfire 110. The infrared and visual images are preferably location-indexed for exact overlay on terrain maps, using GPS data readily available on the UAV 102. Actual fire shape and intensity and vegetation conditions are input periodically to the computer-based fire growth models to correlate the models, and provide a baseline for optional reinitiation of simulations.

The UAV 102 further includes automated flight controls, two-way radio systems for communications with a ground-based remote controller and with other data receivers (the satellite 140, etc.), and at least one processor configurable with instructions such as speed, altitude and location of flight, definition of the target area 112 and number/location of the near-surface-sited sensors 120 to deploy, etc. Mission instructions may be pre-programmed before take-off of the UAV 102, and also updated or amended during flight via commands from the ground-based remote controller.

All of the above discussion applies not only to monitoring a single contiguous wildfire, but also to monitoring a cluster of two or more separate fires within a certain geographic locale—where the two or more fires in the cluster may or may not eventually merge. The spatial extent of fire regimes is such that an outbreak of multiple coexistent wildfires is encountered episodically, and calls for the performance characteristics of a Global Hawk.

Figure 5:
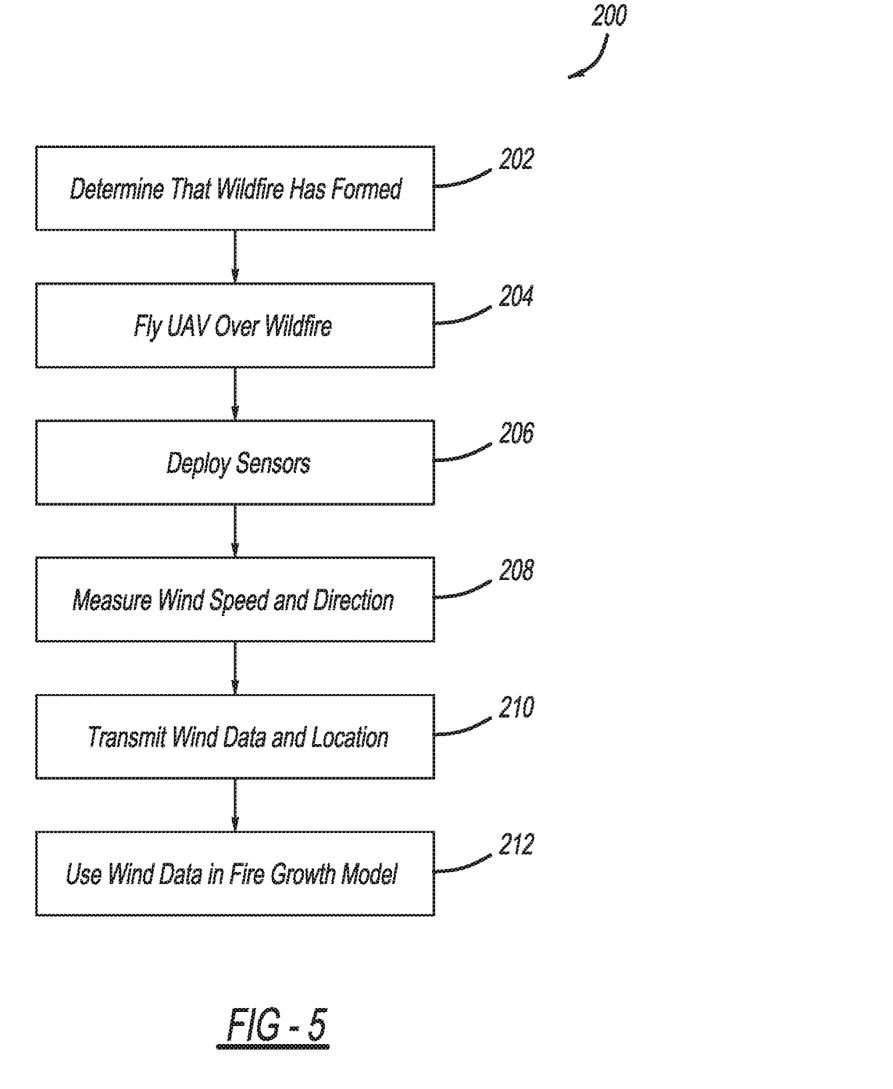
FIG. 5 is a flowchart diagram of a method for providing real-time wind data for a wildfire, according to an embodiment of the present invention.

FIG. 5 is a flowchart diagram 200 of a method for providing real-time wind data for a wildfire using the system 100 discussed above, according to an embodiment of the present invention. At box 202, it is determined that the wildfire 110 has formed and needs to be monitored and managed. Detection and reporting of wildland ignitions are less problematic in an era of extensive satellite constellations, commercial and civil aviation, off-road vehicles, cell phones, wildland-urban intermix and interface, etc. At box 204, the UAV 102 is launched and flown to the location of the wildfire 110, where the UAV 102 remains flying over the target area 112. At box 206, the UAV 102 deploys the near-surface-sited sensors 120 into the target area 112, where the number of the sensors 120 may range from a few to dozens depending on the size of the wildfire 110, whether the wildfire 110 entails a cluster of fires with multiple burn sites, and other factors.

At box 208, the near-surface-sited sensors 120 measure wind speed and direction and optionally other data such as air temperature and pressure and relative humidity. Data may be measured by the dropsonde sensors 120 during descent, and are measured on an ongoing basis (typically for many days) after landing. At box 210, the near-surface-sited sensors 120 transmit the wind data, the other data and location data to the UAV 102 for relaying to fire management authorities. The sensors 120 may also transmit the data to a ground-based receiver instead of, or in addition to, transmitting to the UAV 102. At box 212, the wind and location data, and optionally the other data, are used by the fire management authorities—including use of the data in computer-based fire growth simulation models.

The techniques discussed above for measuring localized wind vectors in and around a wildfire offer many advantages over traditional subjective-estimation-based methods. These advantages include real-time, on-demand deployment of wind sensors to exactly the locations needed for wildfire monitoring, where the near-surface-sited sensors (and/or their replacements) and the circling UAV can readily continue to operate and provide the needed wind data for the duration of a wildfire—even a large-area, long-duration wildland fire. Indeed, fast runs of a large-area long-lived wildland fire under strong spread-aiding winds may be episodic, amid significant-duration intervals of modest growth under relative calm. The local wind data in turn enable modeling and simulation of wildfire growth which can be used to support decision-making regarding the most appropriate response to the wildfire—whether to undertake active firefighting countermeasures or to monitor passively its burning.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A method for measuring wind conditions in and around a large-area wildland fire, said method comprising:
   determining that the wildland fire has formed;
   flying an unmanned aerial vehicle (UAV) above the wildland fire, where the UAV includes a configurable processor and a communications system for communicating with a ground-based remote controller;
   deploying a plurality of sensors from the UAV into a target area within and surrounding the wildland fire, including aiming each of the sensors for a specific landing location such that the plurality of sensors form a prescribed pattern within the target area;
   measuring localized wind data, including wind speed and direction, by each of the sensors; and
   transmitting the wind data and location data by each of the sensors to the UAV for relaying to fire management authorities.

2. The method according to claim 1 wherein the location data transmitted by the sensors is provided by a Global Positioning System (GPS) sensor onboard each of the sensors and includes an elevation or altitude value.

3. The method according to claim 1 wherein, after the sensors have reached ground, the wind data are measured at a height of 1-2 meters above the ground or surface vegetation.

4. The method according to claim 1 wherein the sensors measure and transmit the wind data and the location data during descent, and continue to measure and transmit the wind data and the location data after reaching ground.

5. The method according to claim 1 further comprising measuring additional data by the sensors and transmitting the additional data to the UAV, where the additional data includes air temperature, air pressure, relative humidity and soil moisture.

6. The method according to claim 5 wherein the wind data, the location data and the additional data are used by the fire management authorities, including use as input into a computer-based fire growth prediction model.

7. The method according to claim 1 further comprising measuring size and intensity of actively flaming regions of the wildland fire using infrared sensors on the UAV and relaying data on the actively flaming regions to the fire management authorities.

8. The method according to claim 1 further comprising providing a vegetation inventory of the target area using optical sensors on the UAV and relaying the vegetation inventory to the fire management authorities.

9. The method according to claim 1 wherein the UAV deploys the sensors to, and monitors data from, a plurality of target areas, where each of the target areas includes a different burn zone.

10. The method according to claim 1 further comprising transmitting the wind data and the location data from the UAV to a satellite, a ground station or a ground-based vehicle for relaying to the fire management authorities.

11. The method according to claim 1 further comprising deploying additional sensors at a time after an initial deployment, where the additional sensors are deployed to new areas resulting from growth or shifting of the target area, or the additional sensors are deployed as replacements for initially-deployed sensors which have exhausted their self-powering timespan.

12. The method according to claim 1 wherein the UAV is a Global Hawk high-altitude long-endurance (HALE) UAV.

13. A method for measuring wind conditions in and around a wildfire, said method comprising:
determining that the wildfire has formed;
flying a Global Hawk unmanned aircraft above the wildfire, where the Global Hawk includes a configurable processor and a communications system for communicating with a ground-based remote controller;
deploying a plurality of sensors from the Global Hawk into a target area within and surrounding the wildfire, including aiming each of the sensors for a specific landing location such that the plurality of sensors form a prescribed pattern within the target area;
measuring meteorological condition data by each of the sensors during descent and after landing at its location within the target area;
transmitting the data and a location by each of the sensors to the Global Hawk for relaying to fire management authorities; and
using the data by the fire management authorities in a computer-based fire growth prediction model.

14. The method according to claim 13 wherein the meteorological condition data includes wind speed and direction, air temperature, air pressure and relative humidity, and the location includes an elevation or altitude value.

15. The method according to claim 13 further capturing infrared images and visual images of the wildfire by the Global Hawk and transmitting the images to the fire management authorities.

16. The method according to claim 13 further comprising continuing flight above the target area and receiving and relaying the data from the sensors, by the Global Hawk, for a period of at least 25 hours before being replaced by a second Global Hawk, where the Global Hawk periodically receives updated mission instructions from the ground-based remote controller, and where the updated mission instructions include a revised definition of the target area and instructions to deploy additional sensors.

17. A method for measuring wind conditions in and around a wildfire, said method comprising flying an unmanned aerial vehicle (UAV) above the wildfire, deploying a plurality of sensors from the UAV into a target area within and surrounding the wildland fire including aiming each of the sensors for a specific landing location such that the plurality of sensors form a prescribed pattern within the target area, measuring meteorological condition data by each of the sensors, and transmitting the data and a location by each of the sensors to the UAV for relaying to fire management authorities.

18. The method according to claim 17 wherein the UAV continues flying above the target area, and receiving and relaying the data from the sensors, for a period of at least 25 hours before being replaced by a second UAV.

19. The method according to claim 18 wherein the UAV periodically receives updated mission instructions from a ground-based remote controller, where the updated mission instructions include a revised definition of the target area and instructions to deploy additional sensors.

* * * * *